United States Patent [19]

Grundei et al.

[11] Patent Number: 4,632,098

[45] Date of Patent: Dec. 30, 1986

[54] ORTHOPEDIC BRACE FOR KNEE JOINTS

[75] Inventors: Hans Grundei; Ernst-Joachim Henssge, both of Lubeck, Fed. Rep. of Germany

[73] Assignee: S & G Implants GmbH, Fed. Rep. of Germany

[22] PCT Filed: Dec. 6, 1984

[86] PCT No.: PGT/DE84/00264

§ 371 Date: Jul. 22, 1985

§ 102(e) Date: Jul. 22, 1985

[87] PCT Pub. No.: WO85/02537

PCT Pub. Date: Jun. 20, 1985

[30] Foreign Application Priority Data

Dec. 8, 1983 [DE] Fed. Rep. of Germany ....... 3344422

[51] Int. Cl.$^4$ ............................................ A61F 5/00

[52] U.S. Cl. .................................... 128/80 C; 128/88

[58] Field of Search ..................... 128/80 C, 80 F, 88, 128/87 R; 2/22, 24

[56] References Cited

U.S. PATENT DOCUMENTS

| | | | |
|---|---|---|---|
| 2,179,903 | 11/1939 | Spears | 128/80 C |
| 2,195,024 | 3/1940 | Bullock | 2/24 X |
| 3,046,981 | 7/1962 | Biggs, Jr. et al. | 128/80 C |
| 3,928,872 | 12/1975 | Johnson | 128/80 C X |

*Primary Examiner*—Stephen F. Husar

*Attorney, Agent, or Firm*—Kinzer, Plyer, Dorn & McEachran

[57] ABSTRACT

The orthopedic brace serves the purpose of splinting and balancing the lateral instability of knee joints and is characterised by a tie-plate intended to be applied to the side of the knee joint having the preponderant instability, which is acted upon by elastic belt straps which lead to fastening points situated above and below as well as laterally offset with respect to the tie-plate. The lines of action of two mutually adjacent belt straps in each cases intersecting each other in the region of the tie-plate.

6 Claims, 2 Drawing Figures

ORTHOPEDIC BRACE FOR KNEE JOINTS

The invention relates to an orthopedic brace for splinting and for balancing the lateral instability of knee joints.

Orthopedic braces of this nature comprise an upper and a lower splint elements of rigid material flanking the upper and lower parts of human legs to a greater or lesser extent, the two splint elements being interconnected by means of a hinge-like joint. It is disadvantageous that an orthopedic brace of this nature does not allow of the natural combined rolling and sliding action of the physiological sequence of motion during the bending and straightening of the human knee, which leads to an unnatural and deleterious strain on the joint-forming bone surfaces of the thigh and lower thigh bones, and causes the onset of muscular atrophy in the upper and lower parts of the leg. This is a consequence of the lateral rigidity of the orthopedic brace. Furthermore, the knee movement imposed on the knee by this already known orthopedic brace results in the disadvantage that the patient finds it unpleasant to wear the orthopedic brace, in particular also because of the lateral rigidity of the orthopedic brace.

The object of the invention consists in devising an orthopedic brace of the kind defined in the foregoing, which allows of the lateral sequence of motion of the knee and is pleasant to wear.

The solution to this problem is based on the orthopedic brace specified and is characterised by a tie-plate intended to be applied on the knee joint side having the preponderant instability and acted upon by elastic belt straps which lead to fastening points situated offset above and below as well as laterally with respect to the tie-plate, the lines of action of two mutually adjacent belt straps in each case intersecting each other in the region of the tie-plate.

Thanks to this solution, the natural sequence of motion of the joint-forming bone surfaces of the thigh and lower thigh bones is assured under satisfactory balancing of the lateral instability of the knee joint, since no movement of any kind is imposed on the knee joint by the orthopedic brace. The muscular atrophy referred to is averted thereby.

Furthermore, the orthopedic brace according to the invention is pleasant to wear, since the tie-plate and the straps acting on the same may yield to the individual movements of all the knee elements playing a part in the movement of the knee in its area, without causing unpleasant feelings of pressure or the like. The patient's willingness to wear the orthopedic brace readily is also promoted thereby, which for its part is beneficial to the curative intent.

The invention is described in the following in respect of an example of embodiment illustrated in the accompanying drawings. In these :

Figure 1:
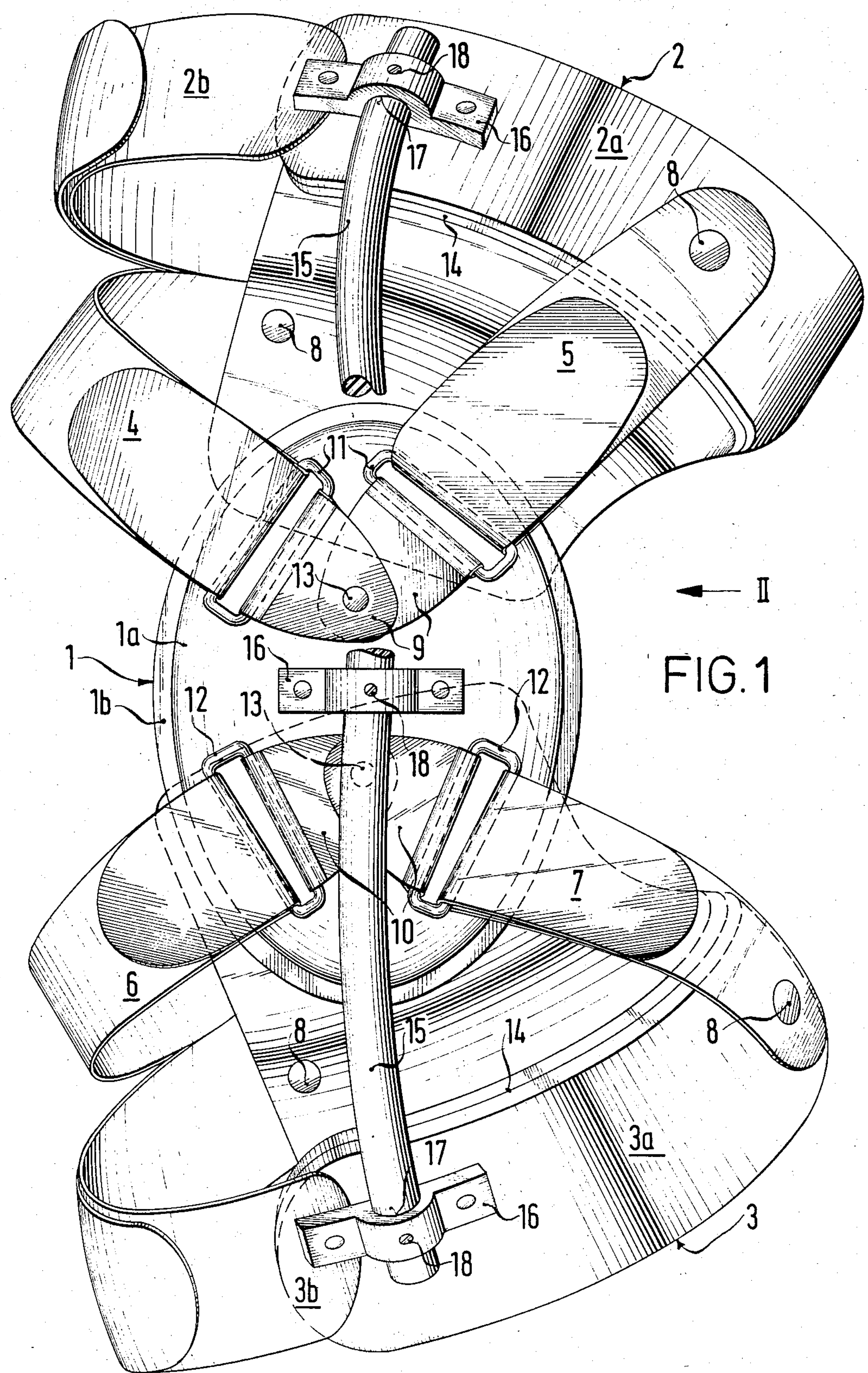
FIG. 1 shows the example of embodiment in a first sideview.
Figure 2:
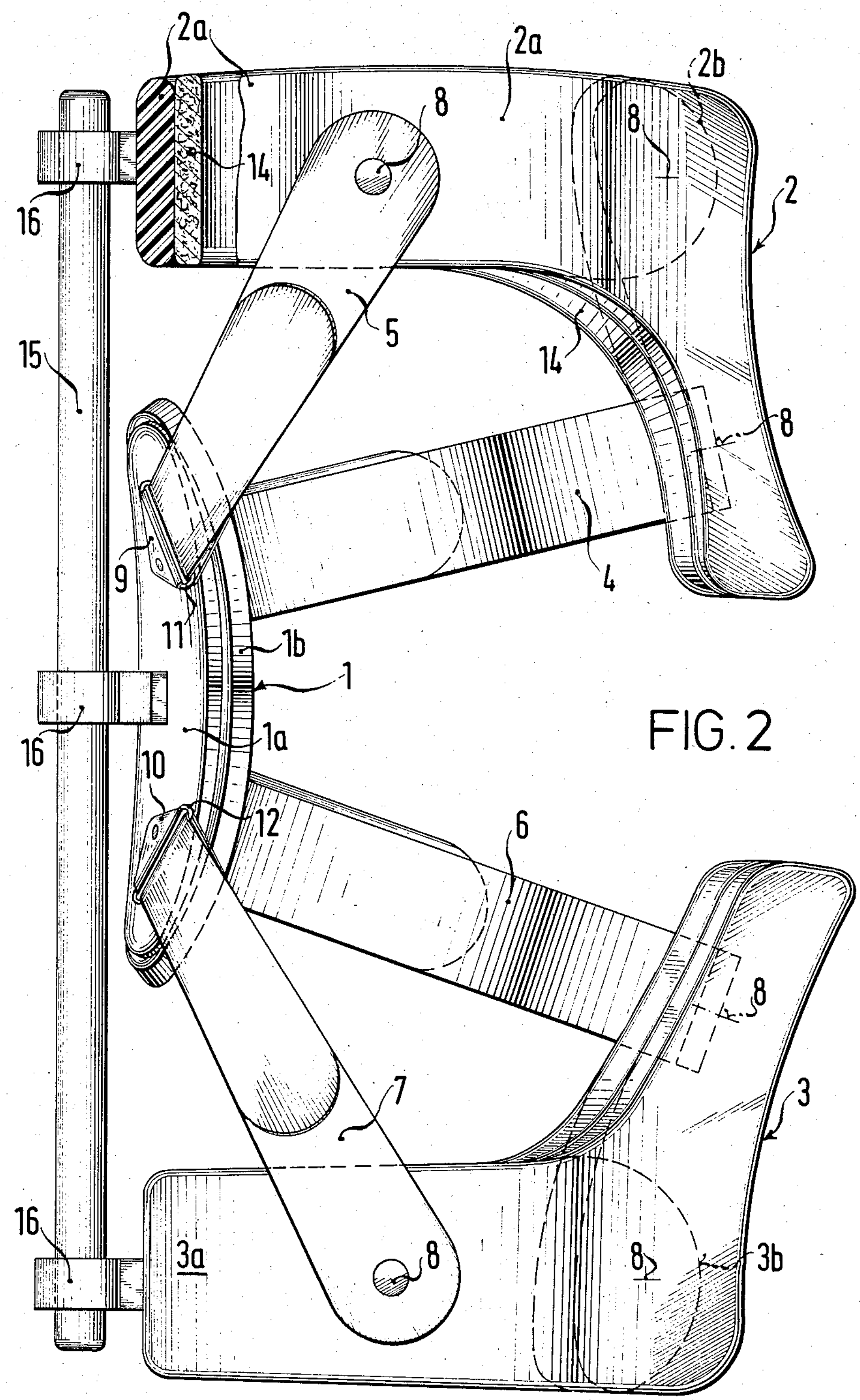
FIG. 2 shows another sideview of the example of embodiment corresponding to the arrow A in FIG. 1.

According to the figures, the orthopedic brace illustrated, which is to be worn by the patient in the region of the knee, for example after plastic knee ligament replacement, comprises a tie-plate 1, an upper shackle 2, a lower shackle 3 and several elastic belt straps 4,5,6 and 7. The belt straps act on the tie-plate 1 on the one hand, and are secured on the other hand to fastening points of the two shackles 2,3, e.g. by means of rivets 8, these points being situated on the shackles offset sideways with respect to the tie-plate, as clearly apparent from FIG. 1. The attachment of the belt straps on the tie-plate may be released and may for example be performed in such manner that splice straps 9,10 are provided with loops 11,12, the belt straps being passed through the loops as illustrated. Two of the splice straps 9 and 10 in each case are fastened to the tie-plate 1, e.g. by means of a rivet 13. Furthermore, the belt straps extend from the shackles 2,3 in the direction towards the tie-plate, in such manner that the lines of action of two mutually adjacent belt straps in each case intersect each other in the region of the tie-plate, as clearly apparent from FIG. 1. In this connection, let it be stated too that the belt straps or rather splice straps are so secured by the rivets 8 and 13, respectively, that a pivotal displacement of these parts is possible around the rivet axis, so that the belt straps may be movable in a particular degree upon donning and wearing the orthopedic brace.

The belt straps 4,5,6 and 7 which are elastic longitudinally as well as transversely, are so formed moreover that they are provided at one side with a so-called "Velcro" closure. The structure and function of a closure design of this kind are generally known, so that a precise description in this connection is superfluous.

The two shackles 2 and 3 each consist of a comparatively rigid material section **2*a* and 3*a*, resp., e. g. of plastics material, and of a flexible lashing strap 2*b* and 3*b*, resp., the one extremity of the strap being secured to the material section, for example by rivetting, whereas its other extremity is releasably fastened to the material section. The latter action may again be performed as described and depicted in connection with the belt straps 4 to 7. It is merely on the score of clearness that this is not illustrated in the drawings. When the orthopedic brace is fitted on the leg of a patient, the material sections 2*a*,3*a* of the shackles 2 and 3 resp., which are rigid in axial direction but flexible in radial direction, in each case partially enflank the thigh and lower leg of the patient, whereas the lashing straps 2*b*,3*b*** which are equally provided with a "Velcro" closure, residually overbridge the leg parts.

The tie-plate 1 comprises a rigid material element **1*a*, e.g. of plastics material, and a resilient padding covering 1*b***, e.g. of an expanded material, which is preferably secured by bonding on the side of the rigid material element facing towards the patient's knee.

The rigid material elements **2*a*,3*a* of the shackles 2 and 3 are also provided at the inner side with a resilient padding covering 14**, e.g. of expanded material, to obtain a pleasant contact of the shackles on the patient's leg.

So that the shackles 2,3 may be kept spaced apart with respect to the tie-plate 1, at least one flexurally elastic bar 15 consisting of plastics material for preference is provided, which is installed on the shackles and on the tie-plate by means of securing elements 16 which are rivetted on. The elements 16, e.g. constructed in the form of a solid journal bearing, comprise a bore 17 through which the bar 15 is pushed. So that the bar may be secured axially in the elements 16, the latter have tapped holes, wherein engage screws 18 which may be acted upon from the outside, which are jammed against the bar. Thanks to this method of immobilising the bar in the elements, the spacing between the shackles and the tie-plate may be set to correspond to the conditions on the patient's knee. The cross-sectional shape of the bar 15 may be circular, but oval too. The latter will be utilised if a greater flexural rigidity of the bar is desirable because of increased instability, the long axis of an oval bar extending substantially parallel to the axis of the patient's knee joint after the orthopedic brace has been fitted.

What is claimed is:

1. An orthopedic brace for splinting and for balancing the lateral instability of knee joints, characterised by a tie-plate (1) intended to be applied on the knee joint side having the preponderant instability and acted upon by elastic belt straps (4,5,6,7) which lead to fastening points (8) positioned offset above and below as well as laterally with respect to the tie-plate (1), the lines of action of two mutually adjacent belt straps in each case intersecting each other in the region of the tie-plate, and further characterised in that the fastening points (8) are provided on shackles (2;3) of which, once the orthopedic brace has been applied, the one (2) partially enflanks the thigh and the other (3) partially enflanks the lower part of the patient's leg, and of which the open portion may be over-bridged by means of releasable straps **(2*b*;3*b*)**.

2. An orthopedic brace according to claim 1, characterised in that the belt straps (4,5;6,7) are secured fixedly on the shackles (2,3) and releasably on the tie-plate (1).

3. An orthopedic brace according to claim 1, characterised in that strap loops (11,12) through which are passed the belt straps (4,5,6,7) acting on the tie-plate, are pivotally arranged on the tie-plate (1).

4. An orthopedic brace according to claim 1, characterised in that the tie-plate (1) and the two shackles (2,3) are held at a preferably variable distance from each other by means of at least one flexurally elastic bar (15) connecting them.

5. An orthopedic brace according to claim 4, characterised in that the bar (15) has an oval cross-section.

6. An orthopedic brace according to claim 4, characterised in that the bar (15) extends through bores (17) of fastening elements (16) which are secured to the tie-plate (1) and the shackles (2,3) and wherein are seated screws (18) which may be actuated from the outside, and with which the bar may be clamped fast in the fastening element in question.

* * * * *